(12) United States Patent
Michaels

(10) Patent No.: US 10,973,444 B1
(45) Date of Patent: Apr. 13, 2021

(54) STANDALONE BLOOD GLUCOSE METER

(71) Applicant: Jeffrey Michaels, Seminole, FL (US)

(72) Inventor: Jeffrey Michaels, Seminole, FL (US)

( * ) Notice: Subject to any disclaimer, the term of this patent is extended or adjusted under 35 U.S.C. 154(b) by 351 days.

(21) Appl. No.: 16/050,024

(22) Filed: Jul. 31, 2018

(51) Int. Cl.
*A61B 5/05* (2021.01)
*A61B 5/145* (2006.01)
*A61B 5/15* (2006.01)

(52) U.S. Cl.
CPC .... *A61B 5/14532* (2013.01); *A61B 5/150022* (2013.01); *A61B 5/150419* (2013.01); *A61B 2562/0295* (2013.01)

(58) Field of Classification Search
CPC .......... A61B 5/14532; A61B 5/150419; A61B 5/150022; A61B 2562/0295; A61B 5/150748; A61B 5/151; A61B 5/157
See application file for complete search history.

(56) References Cited

U.S. PATENT DOCUMENTS

| | | | | |
|---|---|---|---|---|
| 2003/0212347 A1* | 11/2003 | Sohrab | ............ | A61B 5/150809 600/584 |
| 2010/0256526 A1* | 10/2010 | Harttig | ............ | A61B 5/150183 600/583 |
| 2012/0039772 A1* | 2/2012 | Hoenes | ............ | A61B 5/150572 422/535 |
| 2013/0085349 A1* | 4/2013 | Shaanan | .......... | A61B 5/150824 600/301 |
| 2013/0267815 A1* | 10/2013 | Lin | ........................ | A61B 5/157 600/365 |
| 2013/0285807 A1* | 10/2013 | Tounooka | .............. | G16B 99/00 340/539.12 |
| 2016/0128614 A1* | 5/2016 | Ho | ..................... | A61B 5/15113 600/583 |
| 2018/0075222 A1* | 3/2018 | Chen | ..................... | A61B 5/742 |

* cited by examiner

*Primary Examiner* — Navin Natnithithadha
*Assistant Examiner* — Andrey Shostak
(74) *Attorney, Agent, or Firm* — Sanchelima & Associates, P.A.; Christian Sanchelima; Alexander Rodriguez

(57) ABSTRACT

A glucose meter includes a housing, and a first chamber and a second chamber defined in the housing. A first barrel is installed in the first chamber and adapted to accommodate multiple lancets therein. A second barrel is installed in the second chamber and adapted to accommodate multiple test strips therein. Additionally, each of the first and second chamber includes a hinged lid which is lifted to expose the first and second barrel from the top end of the first and second chamber. The hinged lids are actuated by buttons on the housing. The lancets are adapted to prick a user's finger in order to reveal blood. A user then positions the blood on the test strip to be absorbed and tested by the glucose meter.

10 Claims, 2 Drawing Sheets

STANDALONE BLOOD GLUCOSE METER

BACKGROUND OF THE INVENTION

1. Field of the Invention

The present disclosure generally relates to glucose meters, and more particularly, relates to a standalone blood glucose meter which incorporates all components needed to conduct glucose measurement test in a single unit.

2. Description of the Related Art

As patients with diabetes have increased drastically in past few decades, portable and simple blood glucose meters are required to obtain blood glucose data for the treatment and care of the diabetic patients. The blood glucose data is obtained by measuring the concentration of the glucose contained in the blood. A conventional blood glucose meter, generally, includes three separate components, namely a lancet and a lancet pen, test strips and a glucose meter unit. Typically, the glucose meter unit has a large-sized body, and the lancets and test strips are stored in separate cases, so that while those being carried by a user or being stored in the cases, some components may be lost frequently. Now, even if one of the components of the blood glucose meter is lost, it becomes impossible to perform the blood glucose monitoring, which may be a risk for the patient who may need to measure his/her blood glucose at a given time.

Furthermore, to use the conventional glucose meter; first, the person needs to remove the cap on the lancet pen to expose the small slot in which the lancet is placed. Second, a small cap needs to be twisted off the lancet to expose the needle, then the pen cap is replaced over the lancet, a plunger on the back of the lancet pen needs to be pushed to set the lancet, and a small button on the side of the pen is pushed to activate the lancet to pierce the finger in order to have the blood come out of the finger to be tested. Third, a small test strip needs to be placed into a small slot on the glucose meter to test the blood. Fourth, after the blood is tested, the test strip needs to be removed from the slot and discarded. Fifth, the cap of the lancet pen needs to be taken off again, the small cap of the lancet is put back over the needle to avoid any accidental sticks, and the small lancet is taken out of the slot and discarded.

The above discussed steps all needs to be performed sequentially and manually which is inconvenient and may even be complicated for some users. Carrying out these multiple steps may also lead to a longer time which may cause the blood to be exposed to air, and thus result in inaccurate measurements. Further, these intricate steps make it really difficult for the persons suffering from medical conditions, such as neuropathy, tremors, arthritis in their hands, limited dexterity and poor eyesight due diabetes, age or muscular degeneration, to measure their blood glucose levels regularly. For instance, it may be difficult for visually impaired people to align the components, like needle with the slot, at the time of measurement.

Therefore, there is a need of a standalone glucose meter which can integrate the lancet mechanism and the test strips in one single unit and provide convenient procedure for performing glucose level measurement operation.

SUMMARY OF THE INVENTION

It is one of the main objectives of the present invention to provide a glucose meter which incorporates all components needed to conduct blood glucose measurement test in a single unit.

It is another objective of the present invention to provide a glucose meter which is simple to use without needing much dexterity on part of the user to conduct the blood glucose measurement test.

It is yet another objective of the present invention to provide a glucose meter which is of relatively simple design, ergonomic, durable, cost-effective and further easy to manufacture.

Further objects of the invention will be brought out in the following part of the specification, wherein detailed description is for the purpose of fully disclosing the invention without placing any limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Illustrative embodiments of the present invention are described below. The following explanation provides specific details for a thorough understanding of and enabling description for these embodiments. One skilled in the art will understand that the invention may be practiced without such details. In some instances, well-known structures, processes and functions have not been shown or described in detail to avoid unnecessarily obscuring the description of the embodiments.

It shall be noted that unless the context clearly requires otherwise, throughout the description, the words "comprise," "comprising," "include," "including," and the like are to be construed in an inclusive sense as opposed to an exclusive or exhaustive sense; that is to say, in the sense of "including, but not limited to." Words using the singular or plural number also include the plural or singular number, respectively while adhering to the concepts of the present invention. Furthermore, references to "one embodiment" and "an embodiment" are not intended to be interpreted as excluding the existence of additional embodiments that also incorporate the recited features.

Figure 1:
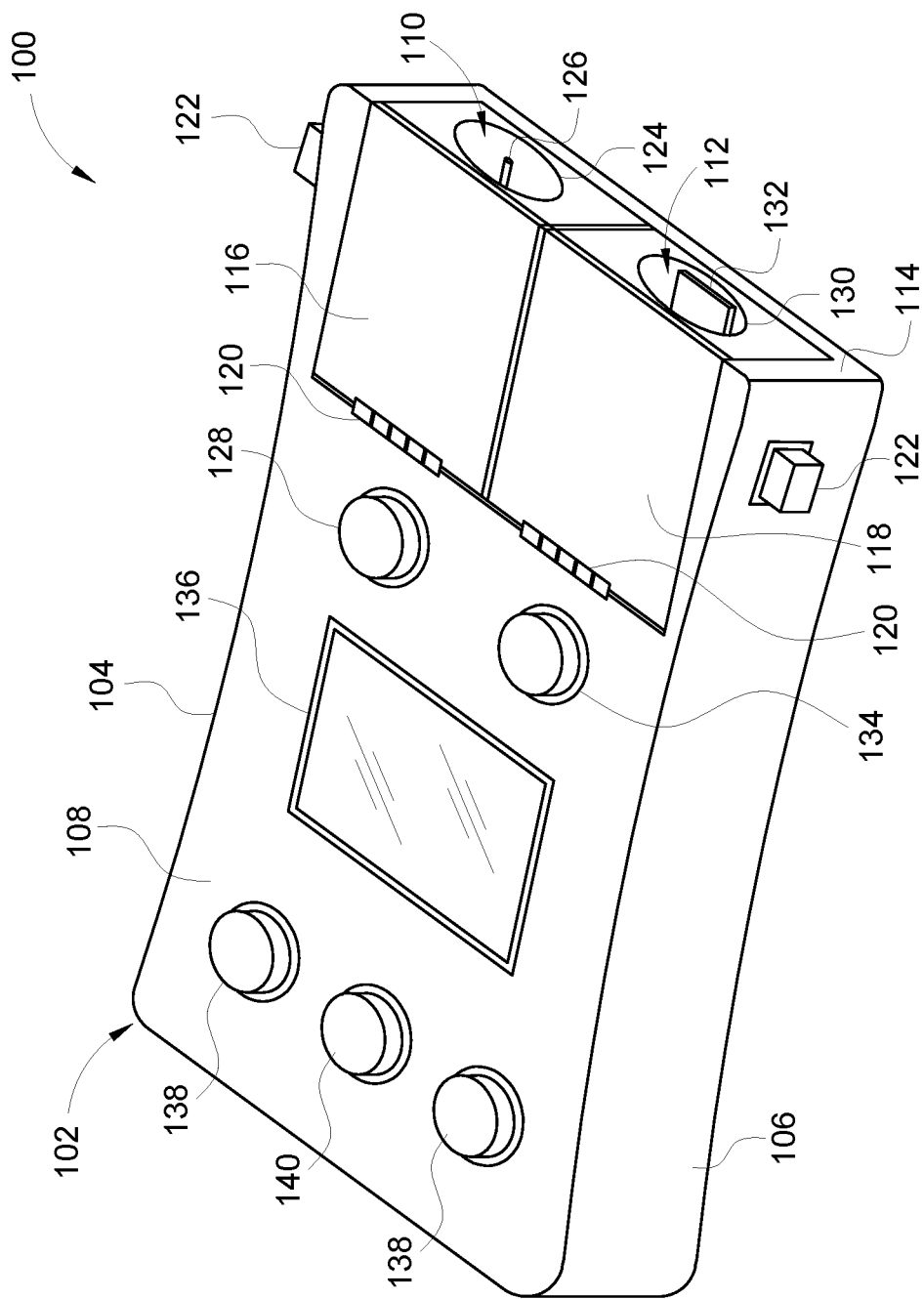
FIG. 1 illustrates a diagrammatic top perspective view of a glucose meter 100 with two chambers 110 and 112 in which the user may insert a finger for testing glucose level thereof, in accordance with one or more embodiments of the present invention.

Referring to the drawings, FIG. 1 illustrates a diagrammatic view of a glucose meter (referred generally by the numeral 100), in accordance with one or more embodiments of the present invention. The glucose meter 100 is a medical device and can be used for determining the approximate concentration of glucose in the blood. As illustrated, the glucose meter 100 includes a housing 102 to incorporate various components thereof. The glucose meter 100 of the present disclosure is a standalone unit with all components needed to conduct glucose measurement test integrated in the housing 102 thereof. The housing 102 may, generally, have a rectangular shape with suitable dimensions to incorporate the various components required for operation thereof. In an exemplary configuration, the housing 102 may have dimensions with height of about 1 to 1.5 inches, length of about 4.5 to 5.5 inches, and width of about 3 to 3.5 inches at its widest and 2 to 2.5 inches at its smallest. The housing 102 may be made of hard plastic or polymer with rubber grips on sides 104 and 106. Further, the bottom surface (not shown) of the housing 102 may be provided with a rubber or polymer coating to keep the glucose meter 100 from sliding or any liquid intrusion when placed on a table/desk. In one or more examples, as illustrated, the housing 102 may have curved profile on the sides 104 and 106, and further the sides 104 and 106 may have rounded corners, which will give the glucose meter 100 a compact appearance and facilitate handling by a user.

Figure 2:
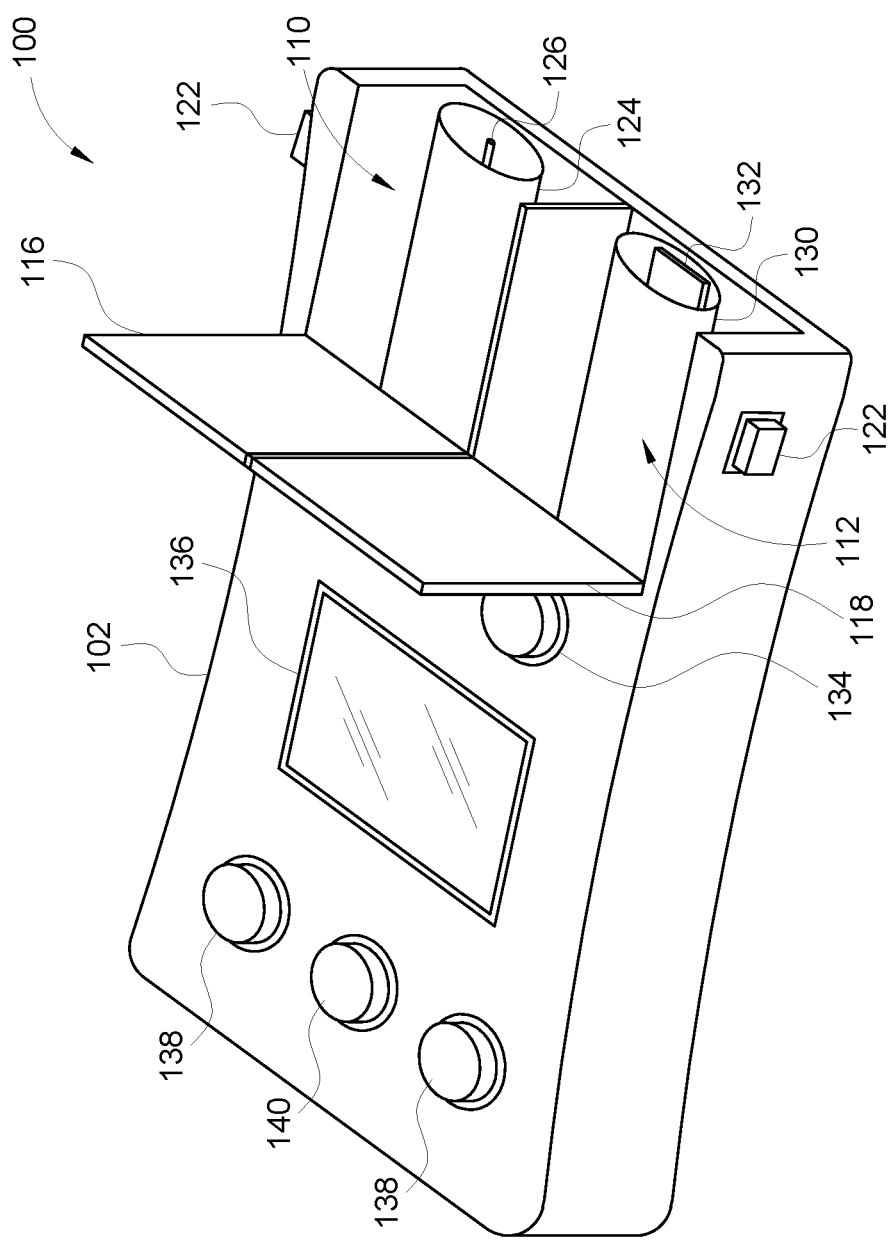
FIG. 2 illustrates a diagrammatic top perspective view of the glucose meter 100 with lids 116 and 118, for the chambers 110 and 112, disposed in open positions to show arrangement inside the chambers 110 and 112, in accordance with one or more embodiments of the present invention.

As illustrated in FIG. 1, the glucose meter 100 includes multiple elements arranged on a top surface 108 thereof. The glucose meter 100 may include two chambers 110 and 112 defined in the housing 102. The chambers 110 and 112 may be in the form of cubical space extruded in the housing 102. The chambers 110 and 112 may be defined proximal to a front face 114 of the housing 102 and provide corresponding openings in the front face 114 for the user to insert his/her finger therein. In some examples, the glucose meter 100 may include two lids 116 and 118 for each of the two chambers 110 and 112, respectively. The lids 116 and 118 may generally be arranged in the same plane as the top surface 108 in closed positions (as depicted in FIG. 1) and coupled thereto by means of hinges 120. Such arrangement may allow the lids 116 and 118 to be disposed in open positions (as depicted in FIG. 2), somewhat similar to opening of a cassette tape recorder, to allow the user to access the inside of the chambers 110 and 112, when required. In an embodiment, the hinges 120 may be spring-loaded hinges and the glucose meter 100 may include buttons 122 arranged on the two sides 104 and 106 which may cause to release the tension in the spring-loaded hinges 120, and thereby allow the user to dispose the one or more of the lids 116 and 118 in open positions by pushing the corresponding button 122.

Referring to FIG. 2, as illustrated, the chamber 110 includes a first barrel 124 adapted to accommodate multiple lancets, such as a lancet 126, shown positioned therein. It may be contemplated that the lancet 126 may be in the form of a needle used to prick a person's finger to cause blood to come out. The lancet 126 is usually meant for single use. The glucose meter 100 of the present disclosure may employ a first barrel mechanism (not shown) which may cause the lancet 126 to move to a front of the first barrel 124 in the chamber 110. The glucose meter 100 may include a first button 128 located on the top surface 108 in line with the first chamber 110, which when pressed may activate the first barrel mechanism to cause the lancet 126 to move. It may be understood that the user may place his/her finger in the chamber 110 and press the first button 128, which may result in pricking of the finger by the lancet 126 to draw the blood out.

Further, as illustrated, the chamber 112 includes a second barrel 130 adapted to accommodate multiple test strips, such as a test strip 132, shown positioned therein. It may be contemplated that the test strip 132 may be in the form of a strip which may absorb a portion of blood in contact therewith. The test strip 132 is usually meant for single use. The glucose meter 100 of the present disclosure may employ a second barrel mechanism (not shown) which may cause the test strip 132 to move to a front of the second barrel 130 in the chamber 112. The glucose meter 100 may include a second button 134 located on the top surface 108 in line with the second chamber 112, which when pressed may activate the second barrel mechanism to cause the test strip 132 to move. It may be understood that the user may place his/her finger in the chamber 112 and press the second button 134, which may result in absorption of the blood, by the test strip 132, from the placed finger in the chamber 112 for glucose level testing purposes.

Further, the glucose meter 100 may include the required electronic circuitry (not shown) arranged inside the housing 102 to determine the glucose level based on the blood absorbed in the test strip 132. Such testing circuitry is well known in the art and thus have not been described herein for the brevity of the present disclosure. It may be understood that the arrangement of the first chamber 110 and the second chamber 112 may allow the user to replace the corresponding barrels 124 and 130 to replenish the lancets 126 and the test strips 132 after use of each of the available multiple units thereof. It may be contemplated by a person skilled in the art that the first and second barrel mechanisms may utilize some form of rotating arrangement, for example by implementation of small motors, to cause the movement of the corresponding components in the respective chambers, on activation via the corresponding button. The barrel mechanisms may further employ gears and guiding grooves arranged in the respective chambers for the said purpose. The barrel mechanisms may further be able to replace the used lancet or the used test strip after each use. Such barrel mechanism may be contemplated by a person skilled in the art and thus have not been described herein. Furthermore, in some alternate examples, instead of a test strip, the glucose meter 100 may employ a pipette/capillary tube for drawing blood for testing purposes.

The glucose meter 100 may further include a display screen 136 provided on the top surface 108 of the housing 102. The display screen 136 may be used for displaying the numeral readings indicative of the glucose level, as received from the electronic circuitry, thereon. The display screen 136 may be any suitable LCD panel as known in the art. In some examples, the glucose meter 100 may also include an audio device (not shown) configured to provide an audio read-out of the numeral reading indicative of the measured glucose level, to help patients with eye-sight problems. Further, in some examples, the glucose meter 100 may include two toggle switches 138 which may be used for changing the parameters being currently displayed on the display screen 136, for example, from the last glucose level reading, to date and time, to menu for setting the date and time for the glucose meter 100 and so forth. Further, the glucose meter 100 may include an ON/OFF switch 140 to turn ON and turn OFF the glucose meter 100, as desired. It may be understood that the switch 140 may cause a battery (not shown) located inside the housing 102 to supply electric power for the various components, including the barrel mechanism and electronic test circuitry, of the glucose meter 100.

The glucose meter 100 of the present disclosure may be easily operated by a user for measuring his/her or someone else's blood glucose level. For measuring own blood glucose level, the user may, first, place his/her finger in the first chamber 110 and press the first button 128. This may cause the lancet 126 to move towards front of the first chamber 110 and thereby prick the finger. The user may, then, place his/her finger in the second chamber 112 and press the second button 134. This may cause the test strip 132 to move towards front of the second chamber 112 and thereby absorb blood from the finger for testing purposes. Therefore, the glucose meter 100 of the present disclosure eliminates the multiple intricate steps as may be required by the conventional devices for blood glucose level testing purposes. For next use, the glucose meter 100 may itself replace the lancet and the test strip therein. Further, the user may simply replace the barrels 124 and 130 after a fixed number of uses of the glucose meter 100 to replenish the lancet and the test strip therein. It may be contemplated that the chambers 110 and 112 may be cleaned and sanitized, where the finger touches, after use by an alcohol wipe or the like.

In some examples, the glucose meter 100 may further include a memory for storing measured blood glucose values, exercises and meals, along with other related data such as the corresponding dates, time of day, and duration of each, and the units that were used as these values and events were measured. The glucose meter 100, via the display screen 136 and switches 138, allow the user to specify which of the stored values to display or functions to access. The glucose meter 100 of the present disclosure is designed for single-hand use and thus make it more convenient for the user to test own blood glucose level. The glucose meter 100 can be handheld or can be set on a table/desk to easily have access to the front face 114 thereof for positioning the finger therein. The glucose meter 100 can assist users who have diabetes in addition to other medical conditions, such as neuropathy, tremors, arthritis in their hands, limited dexterity and poor eyesight due diabetes, age or muscular degeneration to measure their blood glucose levels conveniently, as there will be no need to align the components, like needle with the slot, at the time of measurement as required in conventional devices.

The glucose meter 100 of the present disclosure is a portable blood glucose monitoring device with all required components integrated into a single unit for testing blood glucose level. The glucose meter 100 acts as a lancet pen, collects the blood, and measures the glucose level in one unit. The lancets 126 and the test strips 132 will each be in self-contained barrels which hold multiple units thereof. The glucose meter 100 is of a suitable size for transport in a handbag or clothing pocket of the user, for portability. The glucose meter 100 may be provided with distinctly marked indented areas on the front face 114 for guiding the use to positon the finger into one of the chambers 110 and 112 while operating the unit. One indented area will be marked for "lancet" and other for "test strip" as per location of the chambers 110 and 112. In some examples, the glucose meter 100 may further include means to provide analytical functions, including communication with remote clinicians for sharing data about blood glucose levels of the user. The glucose meter 100 of the present disclosure may be employed by diabetic patients, medical staff, emergency response services, and the like.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense in any manner.

What is claimed is:

1. A glucose meter, comprising:
   a housing having a substantially rectangular shape, said housing including lateral sidewalls each having a curved profile with rounded corners, said curved profile being a concave curved profile, said housing further including a top surface and a front face;
   a first chamber and a second chamber defined in the housing, wherein said first chamber and said second chamber each are a cuboidal space in the housing, said first and second chambers each positioned proximal to the front face of the housing such that the first and second chambers are constantly exposed from the front face of said housing;
   a first barrel installed in the first chamber and accommodating a lancet therein, wherein said first barrel is a cylindrical tubular structure extending within the first chamber and terminating at the front face of said housing, said lancet being nested within said first barrel;
   a second barrel installed in the second chamber and accommodating a test strip therein, wherein said second barrel is a cylindrical tubular structure extending within the second chamber and terminating at the front face of said housing, said test strip being nested within said second barrel;
   a first lid and a second lid provided for said first and second chamber respectively, wherein said first and second lids are arranged on the top surface of said housing, said first and second lids being coupled to the top surface with hinges, wherein said first and second lids are positioned parallel to each other and each terminate at the front face of said housing, wherein said lateral sidewalls of the housing include buttons positioned toward said front face of the housing, wherein said buttons are actuated to engage said first and second lids in an open position thereby providing access to the first and second chambers, said first and second lids extending upwardly from the top surface of the housing when in the open position; and
   electronic circuitry arranged inside the housing and configured to measure a glucose level from blood in the test strip.

2. The glucose meter of claim 1 further comprising a display screen positioned on the top surface of the housing configured to display a numeral reading indicative of the measured glucose level.

3. The glucose meter of claim 2 further comprising a toggle switch to change parameters being currently displayed on the display screen.

4. The glucose meter of claim 2 wherein said display screen is an LCD panel.

5. The glucose meter of claim 1 wherein said first chamber and said second chamber are divided by a wall structure within the housing.

6. The glucose meter of claim 1 wherein said hinges for the first and second lid are spring loaded hinges.

7. The glucose meter of claim 1 further including a power button positioned on the top surface of said housing configured to turn on and turn off the glucose meter.

8. The glucose meter of claim 1 wherein said first lid and said second lid are rectangular in shape.

9. The glucose meter of claim 1 wherein said first lid and said second lid are flush with the top surface of said housing in a closed position.

10. A glucose meter, consisting of:
   a) a housing having a substantially rectangular shape, said housing including lateral sidewalls each having a curved profile with rounded corners, said curved profile being a concave curved profile, said housing further including a top surface and a front face;
   b) a first chamber and a second chamber defined in the housing, wherein said first chamber and said second chamber each are a cuboidal space in the housing, said first and second chambers each positioned proximal to the front face of the housing such that the first and second chambers are constantly exposed from the front face of said housing, said first and second chambers being divided by a wall structure within the housing;

c) a first barrel installed in the first chamber and accommodating a lancet therein, wherein said first barrel is a cylindrical tubular structure extending within the first chamber and terminating at the front face of said housing, said lancet being nested within said first barrel;

d) a second barrel installed in the second chamber and accommodating a test strip therein, wherein said second barrel is a cylindrical tubular structure extending within the second chamber and terminating at the front face of said housing, said test strip being nested within said second barrel;

e) a first lid and a second lid provided for said first and second chamber respectively, wherein said first and second lids are arranged on the top surface of said housing, said first and second lids being coupled to the top surface with spring loaded hinges, wherein said first and second lids are positioned parallel to each other and each terminate at the front face of said housing, wherein said lateral sidewalls of the housing include buttons positioned toward said front face of the housing, wherein said buttons are actuated to engage said first and second lids in an open position thereby providing access to the first and second chambers, said first and second lids extending upwardly from the top surface of the housing when in the open position;

f) electronic circuitry arranged inside the housing and configured to measure a glucose level from blood in the test strip; and g) an LCD display screen positioned on the top surface of the housing, wherein said LCD display screen is configured to display a numeral reading indicative of the measured glucose level, said housing further including a power button positioned above the LCD display screen and configured to power on and power off said electronic circuitry, said housing further including toggle switches positioned on the top surface of the housing above the LCD display screen and configured to change parameters being currently displayed on the display screen.

* * * * *